US007879595B2

(12) United States Patent
Okamoto et al.

(10) Patent No.: US 7,879,595 B2
(45) Date of Patent: Feb. 1, 2011

(54) APPARATUS FOR PERFORMING BIOCHEMICAL PROCESSING USING CONTAINER HAVING WELLS

(75) Inventors: Hideaki Okamoto, Yokohama (JP); Yasuyuki Numajiri, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 1134 days.

(21) Appl. No.: 11/528,601

(22) Filed: Sep. 28, 2006

(65) Prior Publication Data

US 2007/0077648 A1 Apr. 5, 2007

(30) Foreign Application Priority Data

Oct. 4, 2005 (JP) ............................ 2005-291298

(51) Int. Cl.
*C12M 1/34* (2006.01)
*C12M 1/40* (2006.01)

(52) U.S. Cl. .............. 435/287.2; 435/287.3; 435/288.4; 435/303.1; 435/809

(58) Field of Classification Search .............. 435/287.2, 435/288.4, 303.1, 305.2, 305.3, 809, 287.3
See application file for complete search history.

(56) References Cited

U.S. PATENT DOCUMENTS 6,143,250 A * 11/2000 Tajima ....................... 422/102
6,335,166 B1 1/2002 Ammann et al.
7,074,367 B2 7/2006 Lurz et al.
2006/0228268 A1* 10/2006 Heimberg et al. ........... 422/130
2007/0077580 A1 4/2007 Ikeda et al. .................... 435/6
2007/0077646 A1 4/2007 Okamoto ................. 435/288.4
2007/0104619 A1 5/2007 Ishibashi et al. ............ 422/130

FOREIGN PATENT DOCUMENTS

JP 7-107999 4/1995
JP 2000-504231 A 4/2000
JP 2002-513936 A 5/2002
WO WO 0124930 A1 * 4/2001

OTHER PUBLICATIONS

Official Action dated Jun. 1, 2010 in Japanese Application No. 2005-291298.

* cited by examiner

*Primary Examiner*—William H Beisner
(74) *Attorney, Agent, or Firm*—Fitzpatrick, Cella, Harper & Scinto

(57) ABSTRACT

A biochemical processing apparatus includes a thermal cycle section, a processing section for performing a processing not requiring heating or cooling, and a cooling section. These sections are arranged in that order and opposed to a container with a plurality of wells.

2 Claims, 10 Drawing Sheets

APPARATUS FOR PERFORMING BIOCHEMICAL PROCESSING USING CONTAINER HAVING WELLS

BACKGROUND OF THE INVENTION

1. Field of the Invention

The present invention relates to biochemical processing apparatus for biochemically processing analytes, and particularly to a DNA testing apparatus including sections for amplifying and purifying DNA analytes.

2. Description of the Related Art

In order to rapidly and accurately analyze nucleotide sequences or to detect a target nucleic acid in a nucleic acid sample, many approaches have been proposed which use hybridization reactions with probe carriers, such as DNA microarrays. The DNA microarray includes probes having nucleotide sequences that may be complementary to a target nucleic acid and the probes are closely fixed on a solid phase, such as beads or a glass plate. In general, the target nucleic acid is detected through the following steps.

First, a target nucleic acid is extracted from a living body sample, such as blood or urine.

In the second step, the extracted target nucleic acid is amplified by, for example, the PCR (polymerase chain reaction) method. More specifically, a first and a second primer are added to a nucleic acid sample, and the sample is subjected to a thermal cycle in the presence of an enzyme. The first primer is specifically bound to part of the target nucleic acid, and the second primer is specifically bound to part of the complementary nucleic acid to the target nucleic acid. If a double-stranded nucleic acid containing the target nucleic acid is bound with the first and second primers, the double-stranded nucleic acid is amplified by elongation (hereinafter referred to as the first PCR).

After the double-stranded nucleic acid containing the target nucleic acid is sufficiently amplified, components other than the amplified double-stranded nucleic acid, such as unreacted primers and nucleic acid fragments, are removed by purification. For the purification, some techniques have been known. For example, the double-stranded nucleic acid may be adsorbed to magnetic particles, or a column filter may be used.

Then, a third primer is added to the purified nucleic acid sample, followed by a thermal cycle. The third primer has been labeled with an enzyme, a fluorescent or luminescent material, or the like, and is specifically bound to part of the complementary nucleic acid to the target nucleic acid. If the complementary nucleic acid to the target nucleic acid is bound to the third primer, a labeled target nucleic acid is amplified by elongation (hereinafter referred to as the second PCR).

If the nucleic acid sample contains the target nucleic acid, the labeled target nucleic acid is produced. If the nucleic acid sample does not contain the target nucleic acid, the labeled target nucleic acid is not produced.

The nucleic acid sample is brought into contact with a DNA microarray so as to hybridize with the probes in the DNA microarray. If the target nucleic acid complementary to a probe is present, the probe and the target nucleic acid hybridize.

In the third step, the target nucleic acid is detected. The label of the target nucleic acid tells whether the probe has hybridized with the target nucleic acid. Thus, it can be determined whether a specific nucleotide sequence is present or absent.

Japanese Patent Laid-Open No. 7-107999 has disclosed an apparatus for continuously performing these steps. The apparatus includes a movable dispenser that transfers a desired liquid into a container so that a reaction occurs.

Reagents used in biochemical reactors often have to be intentionally prevented from deteriorating. In particular, enzymes important for biochemical reaction may deteriorate at room temperature, and are generally stored at a predetermined temperature or less. If such reagents are used in a limited space in a reactor, a cold storage section for storing the reagents and a reaction section must be closely disposed. Unfortunately, for amplification, the reaction section is subjected to a thermal cycle between about 55° C. and 95° C. If the reaction section is close to the cold storage section, the temperature of the thermal cycle may be conducted to the cold storage section. Furthermore, purification after the amplification may be disadvantageously performed in a limited space.

The apparatus disclosed in Japanese Patent Laid-Open No. 7-107999 includes a purifying section on the left side, a heating section in the middle, and a cold storage section on the right side when viewed from above, and a container is transferred from one section to another. This arrangement increases the width of the apparatus and requires the container to move a long distance, because these sections are apart from each other. Accordingly, it takes a longer time to test.

SUMMARY OF THE INVENTION

The present invention provides a biochemical processing apparatus including a structure including a heating section and a cooling section, and components of the structure are arranged so as to downsize the apparatus and reduce the processing time.

According to an aspect of the invention, a biochemical processing apparatus is provided which performs biochemical processing on an analyte in a container with a plurality of wells. The biochemical processing apparatus includes a support to support the container; a heating section disposed so as to oppose wells used for heating; a cooling section disposed so as to oppose wells used for cold storage; and a processing section that performs a processing not requiring heating or cooling, disposed between the wells to be heated and the wells to be cooled. The heating section, the processing section, and the cooling section are disposed in that order and opposed to the container supported by the support.

In yet another aspect, the present invention relates to a biochemical processing apparatus for performing biochemical processing on an analyte in a container with a plurality of wells, the apparatus including: a support that supports the container; a heating section disposed so as to oppose wells used for heating; a cooling section disposed so as to oppose other wells used for cooling; and a processing section that performs a processing not requiring heating or cooling, the processing section being disposed above wells that are located between the wells used for heating and the wells used for cooling.

Further features of the present invention will become apparent from the following description of exemplary embodiments with reference to the attached drawings.

DESCRIPTION OF THE EMBODIMENTS

Figure 1:
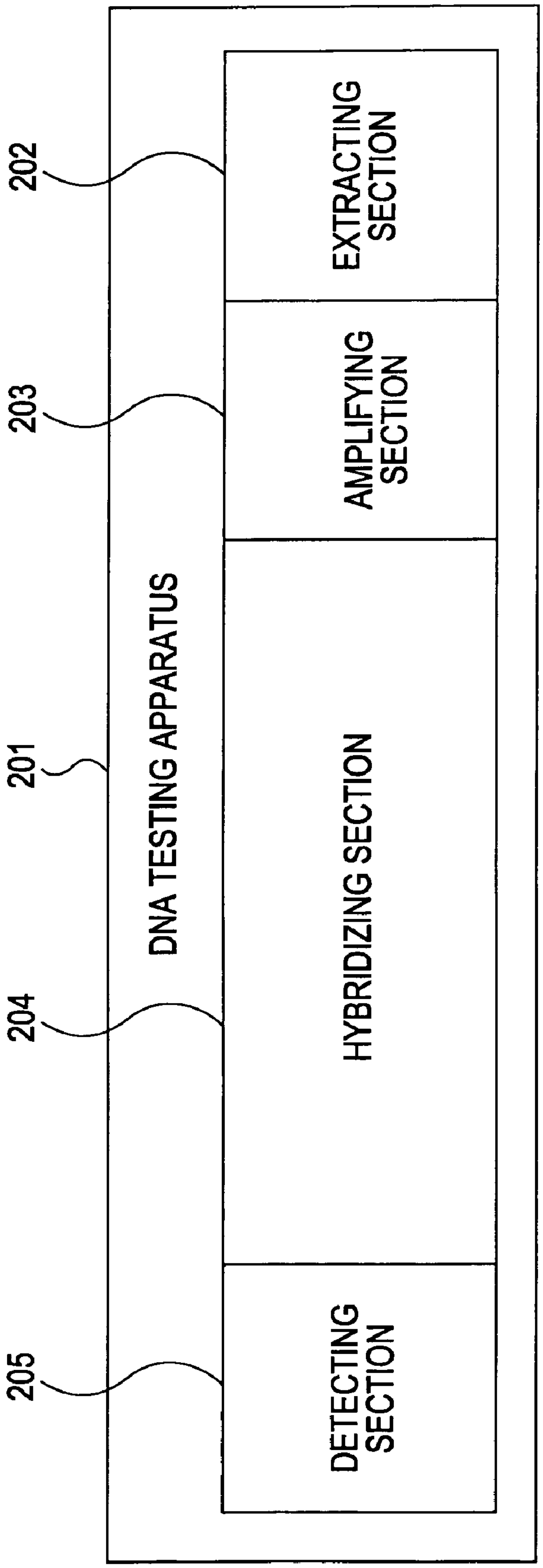
FIG. 1 is a schematic diagram of a DNA testing apparatus according to an embodiment of the present invention.

The present invention will be further described in detail using a DNA testing apparatus being a type of biochemical processing apparatus.

The DNA testing apparatus continuously performs a plurality of steps, such as extraction of an analyte DNA, amplification, and hybridization, and detection. In the following description, a section for amplification will be mainly described.

A commercially available PCR microplate with 96 wells or its similar form with wells can be used as a reaction/storage container having at least a plurality of portions for storing liquid. Reagents used in the PCR process are previously placed in the reaction/storage container. Wells on one side of the container are intended for use for the first and the second PCR; wells in the middle of the container are used for purification; and wells on the other side contain reagents used in purification and the first and second PCR's.

The amplifying section principally includes a thermal cycle section, a purifying section, and a cold storage section. These three sections are located so closely that they can perform their respective functions without shifting the reaction/storage container.

The thermal cycle section includes a thermal cycle block made of a thermally conductive metal, such as aluminium or a copper alloy, and having a plurality of recesses to fit the reaction/storage container and to come into tight contact with the container, and a heating device, such as a Peltier device or a heater. The number of recesses is the same as that of the wells in which the first and the second PCR are performed. The first and the second PCR are performed with the reaction/storage container fitted in the thermal cycle block. In general, the temperature is set at three points: about 92° C., 55° C., and 72° C., and the reaction/storage container is allowed to stand at each temperature for a predetermined time period. This cycle is repeated about 40 times for the first PCR, and about 25 times for the second PCR.

The thermal cycle section also includes a heating unit above the reaction/storage container. The heating unit includes a heating block made of a thermally conductive metal, such as aluminium or a copper alloy, and a heating device, such as a Peltier device and a heater. Heat is applied to the heating block from above to heat the reaction/storage container. The heating block has such a size as it covers only the wells for the first and second PCR's so as not to heat the wells that should be kept cold. Thus, the temperature of the inner walls of the wells in the thermal cycle section increases, and the rising vapor of the solution can be prevented from condensing on the inner walls.

The amplifying section has the purifying section in the region opposing the middle of the reaction/storage container. In the purifying section, purification, which is a processing not requiring heating or cooling, is performed. The purification is performed by a common technique, for example, using magnetic particles and a magnet. The magnetic particles are previously placed in the wells in the purifying section, and the magnet is disposed close to these wells.

A nucleic acid solution, a cleaning liquid, ethanol, and other agents are added step by step in these wells, and then the mixture is stirred to adsorb the nucleic acids to the magnetic particles. Subsequently, the magnet, which is located normally apart from the wells, is brought closer to the purification wells so that the nucleic acids-adsorbing magnetic particles are collected together, and the solution in the purification wells is sucked with the nucleic acids-adsorbing magnetic particles left in the wells. Then, an eluant is added to the wells to separate the nucleic acids from the magnetic particles. The magnet is brought closer to the purification wells to collect the magnetic particles together and the solution except the magnetic particles is sucked. Thus, a purified nucleic acid solution is prepared.

A cold storage section is disposed on the opposite side to the thermal cycle section of the reaction/storage container. The cold storage section includes a cooling block made of a thermally conductive metal, such as aluminium or a copper alloy, and having recesses to fit the reaction/storage container and to come into tight contact with the container, and a Peltier device or the like. The number of recesses is at least the same as that of the wells containing reagents. The periphery of the cooling block is covered with a heat insulator.

Each reagent or solution is transferred from one well to another by a pipette unit. The pipette unit has a removable pipette chip at its end. The pipette unit is replaced as required.

The reagents are stored in the wells at a temperature at which they do not deteriorate until the reagents are used, after the reaction/storage container is set to the apparatus. The temperature for storage is in the range of about 4 to 20° C., and needs to be maintained without varying depending on the temperature (55 to 92° C.) of the closely disposed thermal cycle section.

By disposing the purifying section between the cold storage section and the thermal cycle section, the thermal cycle section and the cold storage section are prevented from thermally affecting each other.

Such arrangement of the thermal cycle section, the cold storage section, and the purifying section, effectively using the limited size of the PCR microplate allows the downsizing of the apparatus, and accordingly reduces the distances across which the pipette unit is shifted to feed or draw the solutions.

In addition to the purifying section, a storage section for storing a reagent, liquid, or the like may be provided between the thermal cycle section and the cold storage section. Preferably, the reagent or liquid to be stored in this section does not need heating or cooling, as with that used in the purifying section. Also, a material not affecting any subsequent step may be stored, as in the case of using a waste container.

First Embodiment

The amplifying section of a DNA testing apparatus according to an embodiment will now be described.

FIG. 1 is a schematic diagram of the DNA testing apparatus.

The DNA testing apparatus 201 includes an extracting section 202 for extracting DNA from a living body, amplifying section 203 for amplifying the DNA, a hybridizing section 204 for binding the amplified DNA to DNA probes, and a detecting section 205 for detecting whether the DNA is bound to the DNA probes. The test process proceeds through the extracting section, the amplifying section, the hybridizing section, and the detecting section in that order.

Figure 2:
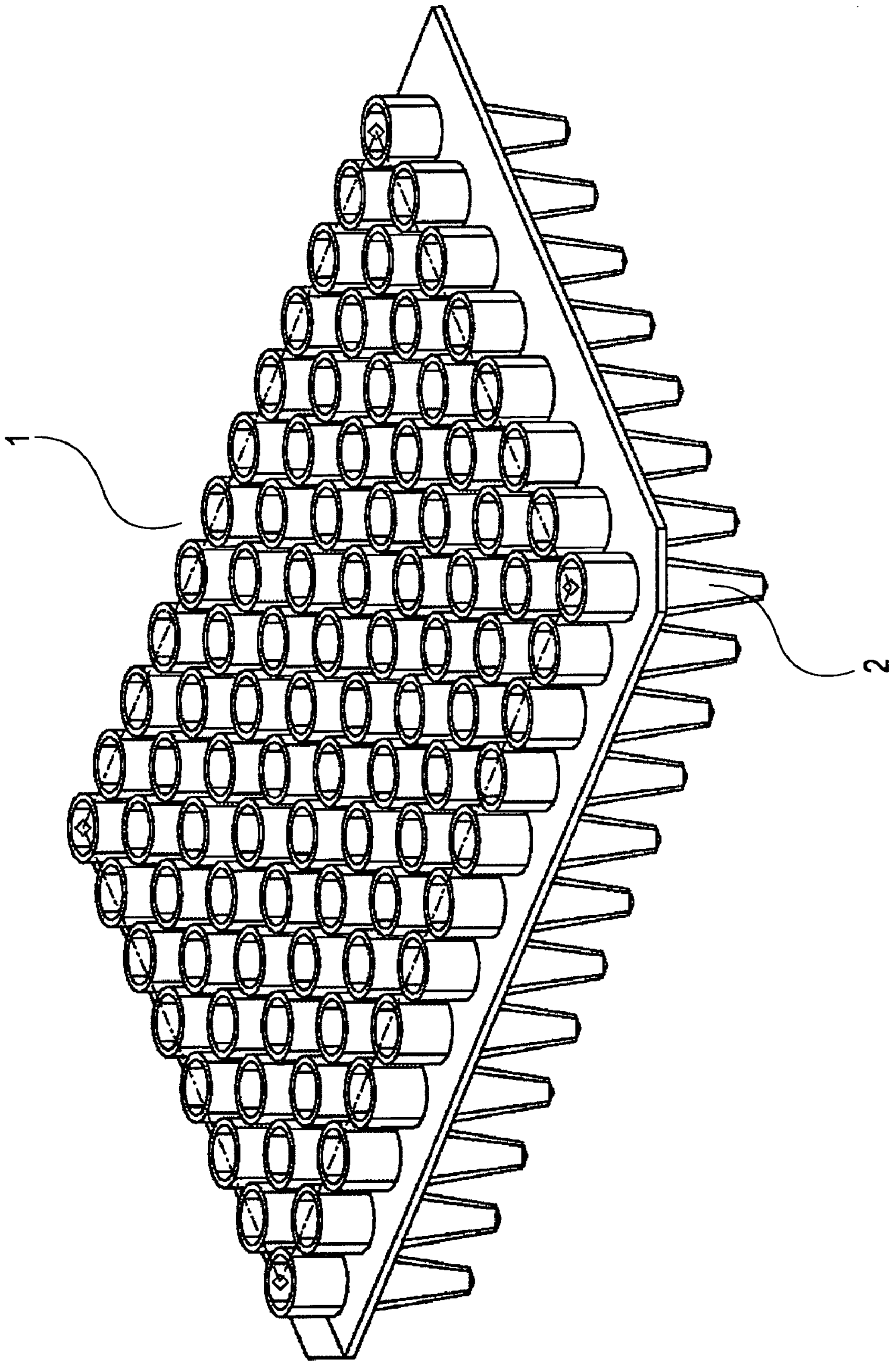
FIG. 2 is a perspective view of wells in a reaction/storage container according to an embodiment of the present invention.

FIG. 2 is a perspective view of wells of a reaction/storage container.

A commercially available propylene PCR microplate 1 or its equivalent is used as the wells, and the wells are arrayed in an 8×12 matrix at a pitch of 9 mm. The bottom end 2 of each well has a shape that can be fitted with the below-described thermal cycle block and cooling block.

Figure 3:
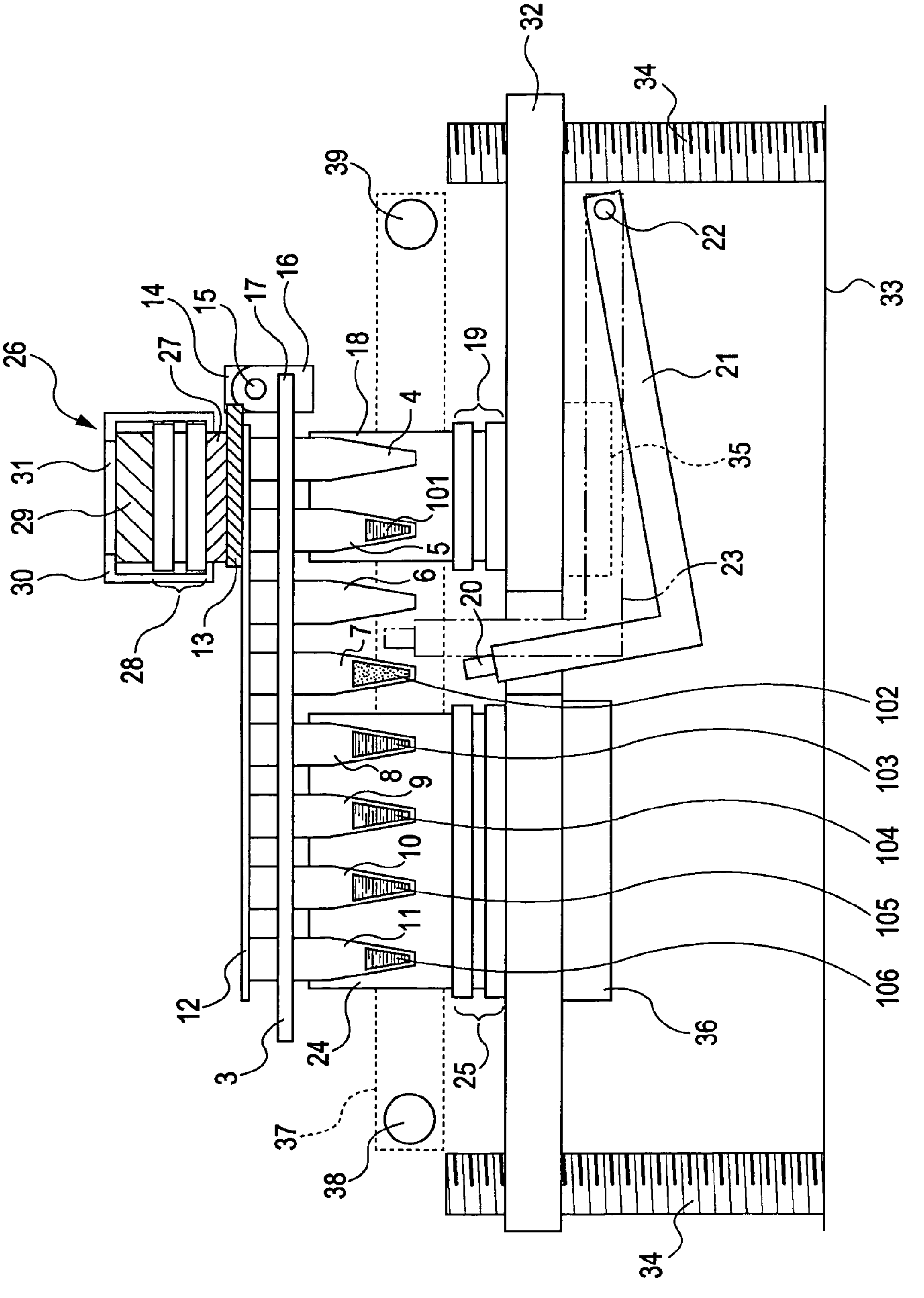
FIG. 3 is a front view of an amplifying section in a DNA testing apparatus according to an embodiment of the present invention.

FIG. 3 is a front view of the amplifying section of the DNA testing apparatus, showing the structure of the reaction/storage container, the arrangement of the wells, and the positional relationship of the thermal cycle section, the cold storage section, and the purifying section.

FIG. 3 shows a state during the first and the second PCR.

In the reaction/storage container 3, the 8×12 wells are divided into 12 groups of 1×8 wells each, and thus 12 analytes can be tested at one time.

The wells are described from the right in FIG. 3. The rightmost wells 4 are used for the second PCR, and are initially empty. The wells 5 in the line to the left of the rightmost wells 4 are used for the first PCR, and in which a solution 101 containing an enzyme and primers has been placed in advance. The wells 6 and 7 in the next two lines are used for purification, and the purification is performed in the wells 7 first. The wells 7 previously contain a magnetic particle liquid 102, and the wells 6 are empty. The wells 8, 9, and 10 in the next three lines contain a cleaning liquid 103, ethanol 104, and an eluant 105, respectively. The wells 11 in the leftmost line contain a solution 106 containing a reagent for the second PCR and a primer. Each line of the wells is constituted of 12 wells, and extends in the direction perpendicular to the sheet of the figure.

The openings of the 96 wells are covered with a laminate film 12 made of, for example, aluminium to prevent contamination. The laminate film 12 is fixed by adhesive bonding, welding, or the like, and is broken with a perforation cutter before solution is drawn out from or added into the well.

The reaction/storage container 3 has a silicon rubber cover 13, a cover-holding member 14, and a fulcrum 15 movably holding the cover 13 and the cover-holding member 14. The fulcrum 15 has a coil spring (not shown) for causing the cover 13 and the cover-holding member 14 to close the wells 4 and 5. The fulcrum 15 is movably held by a bearing 16. If a commercially available PCR microplate is used as the wells, the bearing 16 is fixed to an end 17 of the PCR microplate with an adhesive or a screw. The bearing 16 may be integrated with an equivalent of the PCR microplate.

The cover 13 has such a size as covers only the 24 wells in the two lines of wells 4 and 5, each having 12 wells, and the size is the same as that of the below-described heating block.

The thermal cycle section includes a thermal cycle block 18 made of a thermally conductive metal, such as aluminium or a copper alloy. The thermal cycle block has 24 recesses (holes).

At least one Peltier device 19 is disposed under the thermal cycle block 18 to cool it. The Peltier device 19 and the thermal cycle block 18 are kept in absolute contact with grease (not shown) that is applied between them to ensure heat conduction. As an alternative to the grease, a thermally conductive sheet may be used.

The number of Peltier devices 19 is set so that 12 wells in a line in the reaction/storage container 3 can be uniformly heated.

The wells 4 and 5 for the first and second PCR's oppose the thermal cycle block 18, and the peripheries of the wells 4 and 5 come into tight contact with the inner walls of the recesses of the thermal cycle block 18.

The periphery of the thermal cycle block 18 is covered with a resin heat insulator (not shown) to prevent heat dissipation.

The purifying section includes a magnet 20, a magnet fixing member 21, and a magnet fulcrum 22 that are disposed so that the magnet 20 is located between each pair of adjacent wells 6 and 7 during purification. In the step of purification, the magnet 20 and the magnet fixing member 21 take a position represented by reference numeral 23 in FIG. 3 to collect magnetic particles. Twelve sets of a magnet 20 and a magnet fixing member 21 are rotatably held by the magnet fulcrum 22, corresponding to the respective pairs of wells 6 and 7. The magnet fulcrum 22 is held by a bearing (not shown) provided in the below-described support plate 32. The magnet fixing member 21 is connected to a solenoid (not shown) at the end opposite to the magnet 20. When the magnetic particles are collected on the wall of the well, a current is applied to the solenoid to draw the magnet fixing member 21 so that the magnet 20 is raised to the position 23.

The cold storage section includes a cooling block 24 made of a thermally conductive metal, such as aluminium or a copper alloy, and having 48 recesses (holes).

A Peltier device 25 is disposed under the cooling block 24 to cool it. In order to ensure heat conduction, grease (not shown) is applied between the Peltier device 25 and the cooling block 24 to keep them in absolute contact. As an alternative to the grease, a thermally conductive sheet may be used.

The number of Peltier devices 25 is set so that 12 wells in a line in the reaction/storage container 3 can be uniformly cooled.

The wells 8 to 11 oppose the cooling block 24, and the peripheries of the wells 8 to 11 come into tight contact with the inner walls of the recesses of the cooling block 24.

The periphery of the cooling block 24 is covered with a resin heat insulator (not shown) to prevent the influence of ambient temperature.

The thermal cycle section also includes a heating unit 26 for heating the reaction/storage container 3 from above. The heating unit 26 includes a heating block 27 made of aluminium or a copper alloy and structured so as to cover only the wells 4 and 5 so as not to heat the other wells 6 to 11. At least one Peltier device 28 is provided on the heating block 27. In order to ensure heat conduction, grease (not shown) is applied between the Peltier device 28 and the heating block 27 to keep them in absolute contact.

In addition, a metal cooling block 29 is fixed on the Peltier device 28 with greases between them. The cooling block 29 promotes heat dissipation from the rear surface of the Peltier device 28.

The cooling block 29 is a hollow structure with an inlet and an outlet connected to tubes (not shown). Cooling water runs through the cooling block from the inlet to the outlet.

The heating block 27, the Peltier device 28, and the cooling block 29 are held in a holding member 30 having an opening 31 in the upper surface. The holding member doubles as a heat insulating member.

The heating unit 26 including the heating block 27, the Peltier device 28, the cooling block 29, and the holding member 30 is referred to as a top unit. The top unit 26 can be shifted rightward, in the figure, by driving means (not shown). The top unit 26 has such a length as the top unit 26 can uniformly heat all the 12 wells in a line of the reaction/storage container 3.

The top unit 26 is positioned so as to be in close contact with the wells 4 and 5 of the reaction/storage container 3 and heats them from above during amplification.

The reaction/storage container 3 is fitted in the thermal cycle block 18 and the cooling block 24, and the below-described-support plate 32 is raised to press the reaction/storage container 3 against the top unit 26. Thus, the peripheries of the wells of the reaction/storage container 3 come into tight contact with the thermal cycle block 18 and the cooling block 24, and the thermal conduction to the wells is enhanced.

The entirety of the thermal cycle section, cold storage section, and purifying section is supported by a support plate 32 disposed under the Peltier devices 19 and 25. The support plate 32 is driven in the vertical direction by a lead screw 34 held to a base 33 with a bearing (not shown), a motor (not shown), and a drive transmission system (not shown).

Water cooling blocks 35 and 36 made of a metal are fixed to the lower surface of the support plate 32 with grease between them in the same manner as described above. The water cooling blocks 35 and 36 are provided corresponding to the Peltier devices 19 and 25 respectively, and promote heat dissipation from the rear surfaces of the Peltier devices 19 and 25. The water cooling plate 35 under the Peltier device 19, indicated by dotted line in the figure, is positioned so as not to interfere with the movement of the magnet fixing member 21.

The water cooling blocks 35 and 36 are each a hollow structure with an inlet and an outlet connected to tubes (not shown). Cooling water runs through the water cooling blocks from the inlet to the outlet.

The reaction/storage container 3 is set in a carriage 37 indicated by a dotted line. The carriage 37 is moved back and forth by a lead screw 38 and a guide shaft 39, which extend perpendicular to the sheet of the figure, with a motor (not shown) and a drive transmission system (not shown). The carriage 37 has such a height as the reaction/storage container 3 can be placed in the carriage 37. When the carriage 37 is located in front of the apparatus, the reaction/storage container is set in the carriage 37. When the carriage 37 is moved backward and arrives at a position where the reaction/storage container 3 opposes the thermal cycle section, the cold storage section, and the purifying section, the carriage 37 is stopped. At this point, the support plate 32 is in a lower position than that shown in FIG. 3, not coming into contact with the reaction/storage container 3. Then, the support plate 32 is raised by the lead screw 34 to the position shown in FIG. 3.

The operation of the DNA testing apparatus will now be described.

Analytes in each row of the wells are processed in the same manner, and the following description will describe how an analyte is processed using 8 wells in a row.

Figure 4:
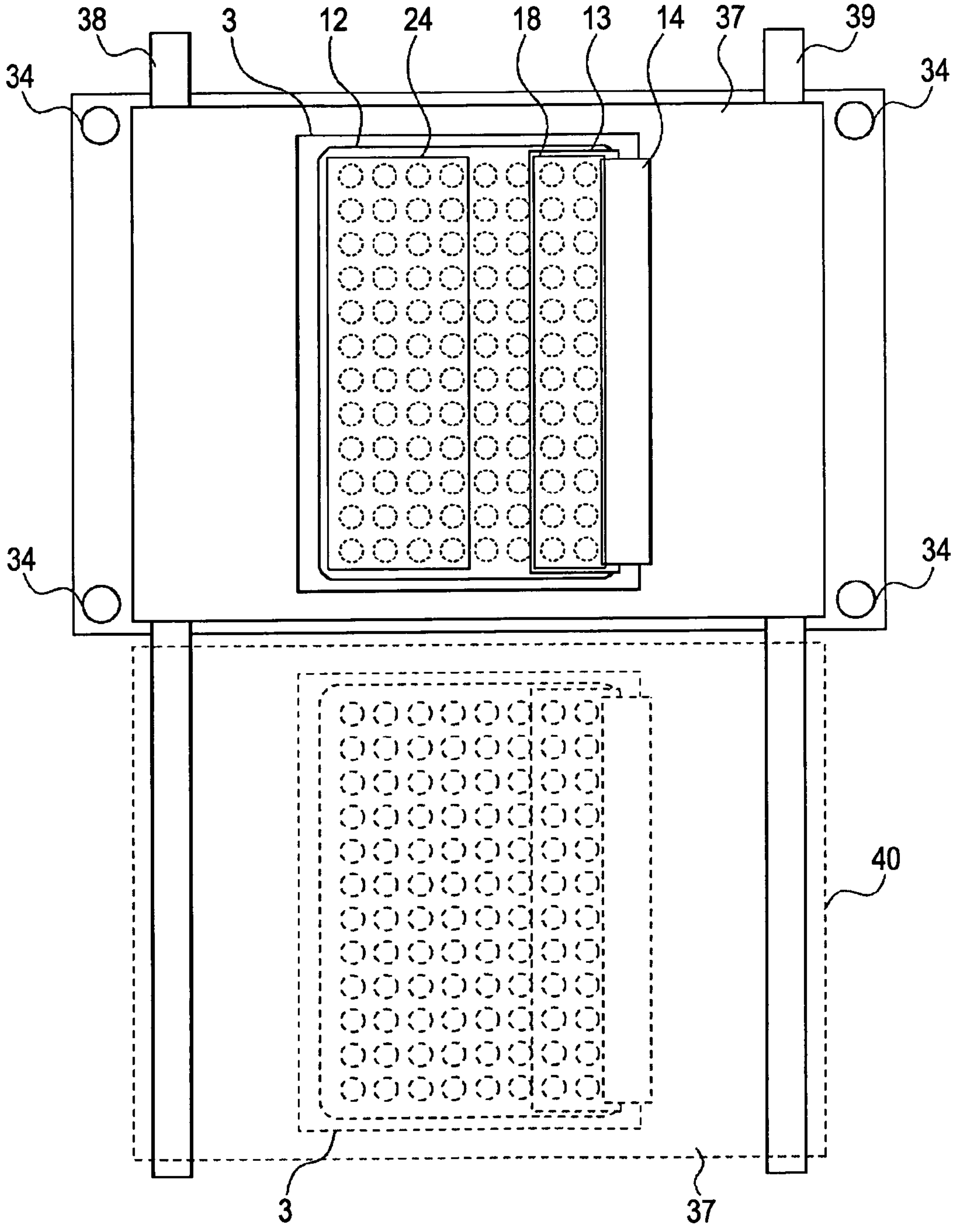
FIG. 4 is a top view of an amplifying section of the DNA testing apparatus.

FIG. 4 is a top view of the amplifying section shown in FIG. 3, showing substantial parts except the top unit 26.

When a user sets the reaction/storage container 3 in the carriage 37 in the position indicated by a dotted line 40, a driving motor (not shown) and the lead screw 38 convey the reaction/storage container 3 backward (upper side in FIG. 4). On arriving at the position indicated by solid lines, the support plate 32 is raised into a state shown in FIG. 5 by the lead screw 38.

Figure 5:
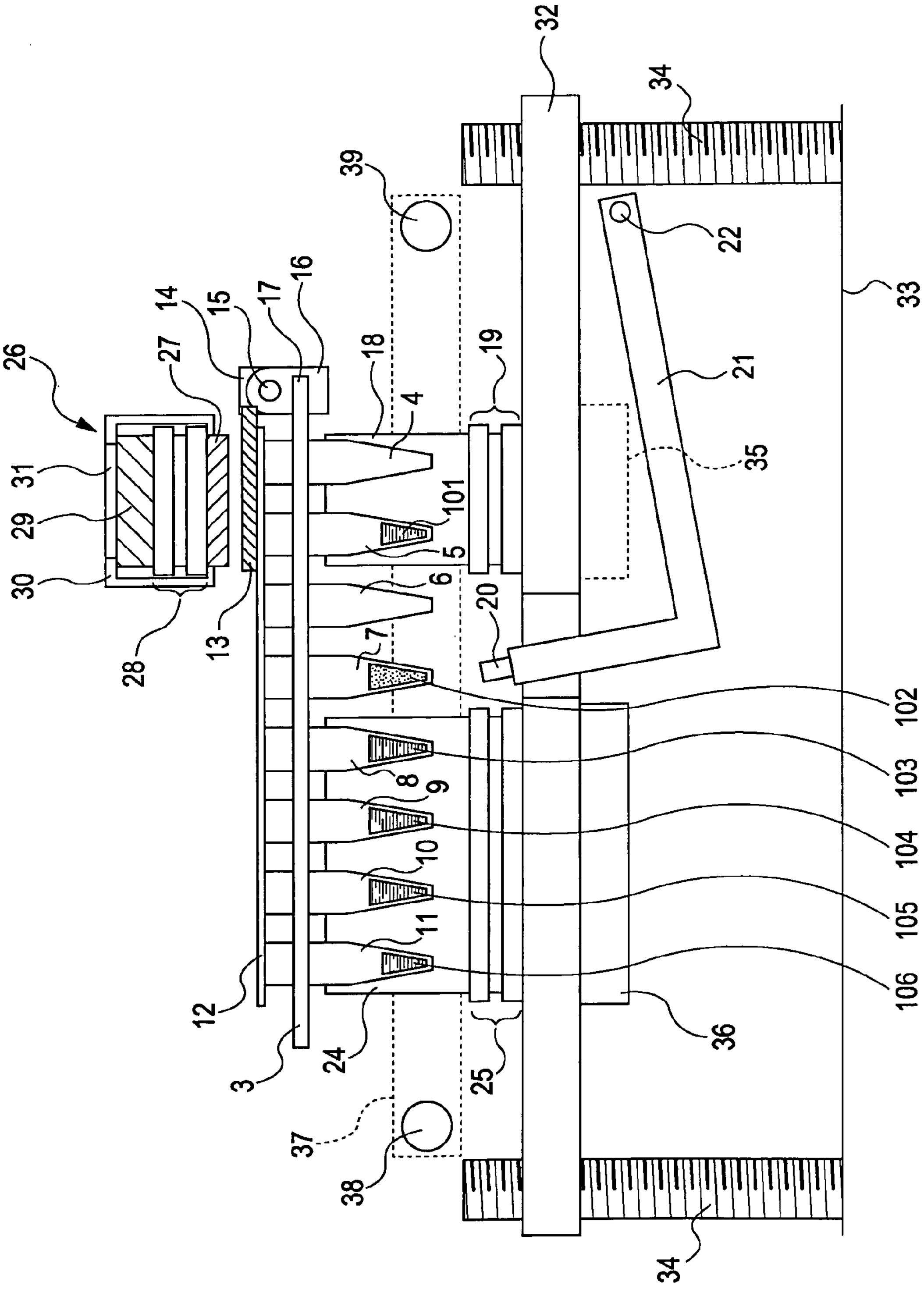
FIG. 5 is a front view of the amplifying section in a state before amplification.

FIG. 5 shows the state where the support plate 32 lies slightly lower than the state shown in FIG. 3, with the heating block 27 in no contact with the cover 13.

A solution containing nucleic acids extracted from a living body, such as blood or urine in the extracting section (not shown) is transferred to the well 5.

For the transfer of the nucleic acid solution, a pipette is used.

Figure 6:
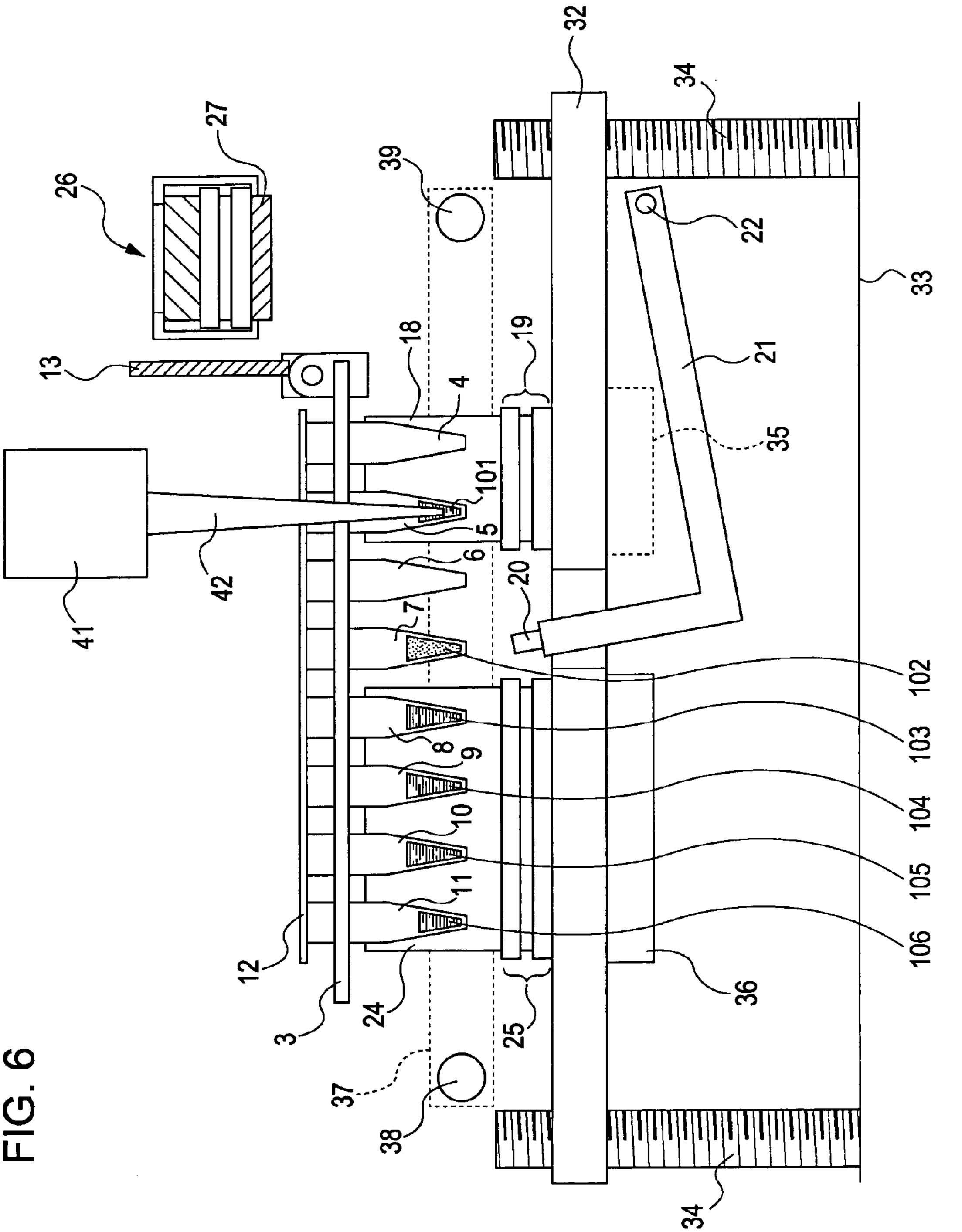
FIG. 6 is a front view of the amplifying section in a state where a nucleic acid solution is discharged.

FIG. 6 shows a state where the nucleic acid solution is discharged into the well 5 from the pipette.

Specifically, the transfer is performed by a pipette unit 41. The pipette unit 41 includes a removable pipette chip and a pipette carrier (not shown) including a motor and a lead screw. The pipette chip 42 is removably attached to an end of the pipette unit, and through which solution is fed, discharged, and stirred. The pipette unit 41 can be shifted back and forth, from side to side, and vertically by the pipette carrier.

In addition, a cutter (not shown) for cutting a hole in the film covering the well is provided on the right side of the pipette chip 42 in the figure. In the vicinity of the pipette unit 41, a pipette chip holder (not shown) is provided for holding virgin pipette chips, and a waste container (not shown) is also provided for used pipette chips. The cutter is transported to a predetermined position by the pipette carrier.

A hole is previously cut in the film 12 in the region corresponding to the well 5 with the cutter so that the pipette chip 42 can be inserted into the well 5 through the hole.

Before cutting the hole, the top unit 26 and the cover 13 are shifted rightward and rotated 90° in the clockwise direction by a driving mechanism (not shown) to open the wells 4 and 5.

The pipette chip 42 sucks the nucleic acid solution from the extracting section disposed on the right side of the figure. The pipette chip 42 containing the solution is shifted over the well 5 and lowered to be inserted into the well 5 to a predetermined depth. Then, the nucleic acid solution is discharged in the well 5.

Subsequently, the suction and discharge of the solution is repeated a predetermined number of times so as to mix the solution sufficiently with the previously added reagents, with the pipette chip kept in the well 5.

After completion of mixing, the pipette unit 41 is moved away from the reaction/storage container 3, and the top unit 26 and the cover 13 are brought into the state shown in FIG. 5.

Then, the support plate 32 is raised to come into the state shown in FIG. 3 by the lead screw 34.

At this point, the support plate 32 is moved toward the top unit 26, and accordingly the cover 13 is pressed at a force of 50 to 100 gf per well, or at a higher force in some cases.

The first PCR is started in the state shown in FIG. 3. A thermal cycle of 92° C., 55° C., and 72° C. for respective predetermined time periods is repeated a predetermined number of times, thereby amplifying the nucleic acids in the well 5. The cold storage section is kept at a temperature at which the reagents do not deteriorate, for example, at about 4° C., during the first PCR. The thermal cycle section (wells 4 and 5) and the cold storage section (wells 8 to 11) are each covered with a heat insulator (not shown) and are separated with a distance by the purifying section (wells 6 and 7).

This arrangement prevents the thermal cycle section and the cold storage section from thermally affecting each other.

After completion of the first PCR, purification is started.

Figure 7:
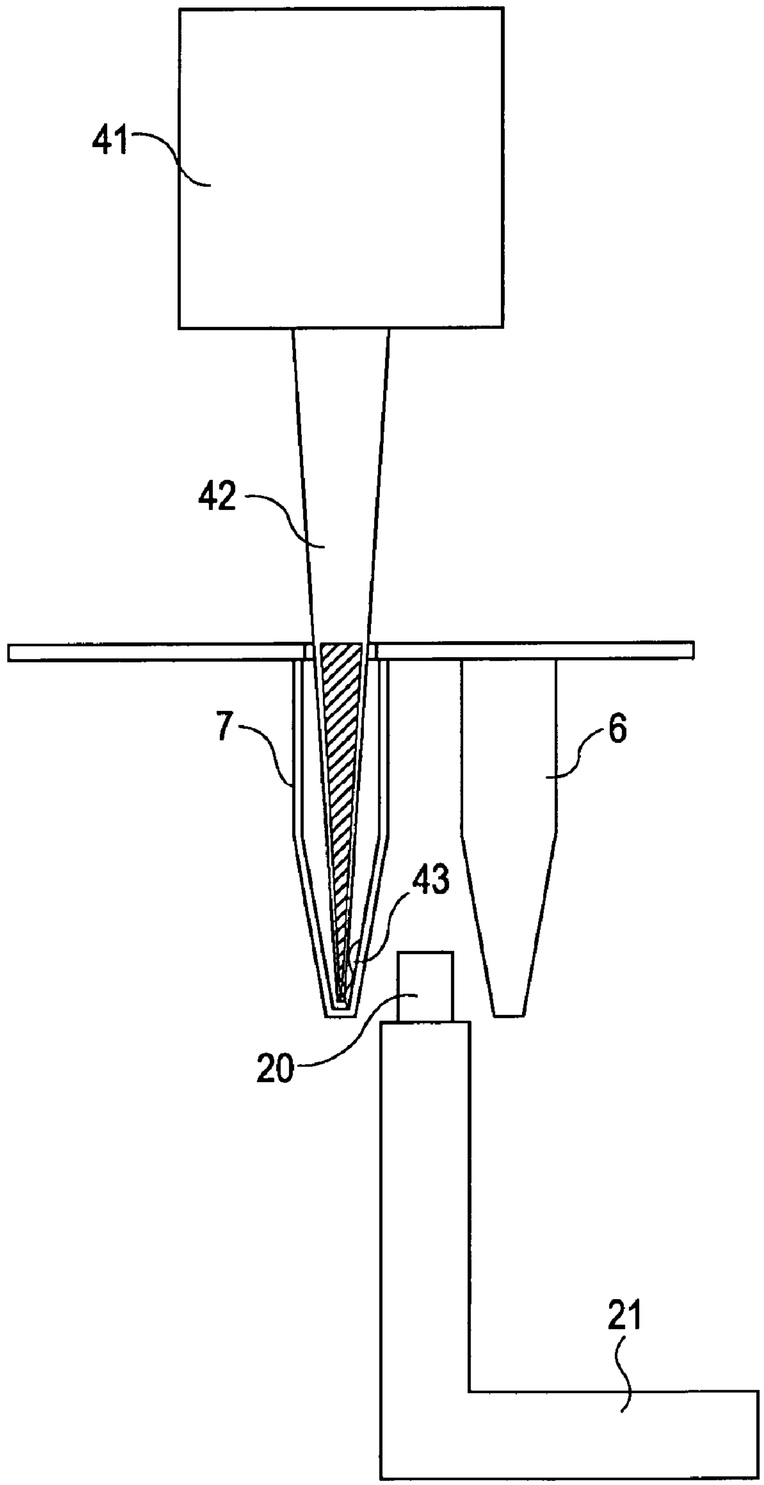
FIG. 7 is a representation of a purification step.

FIG. 7 shows a state where the residue of the amplification product is sucked into the pipette chip 42 after the collection by magnet 20 of magnetic particles 43 that have adsorbed nucleic acids.

The solution in the well 5 is sucked into the pipette chip 42 and subsequently discharged into the purification well 7 (whose sealing film has been cut in advance).

Then, the solution sucked from the well 5 is added to and mixed with the magnetic particle liquid 102 previously placed in the well 7 using the pipette chip 42 so that the magnetic particles sufficiently adsorb the nucleic acids. Subsequently, the magnet 20 is raised to the position shown in FIG. 7 to collect the nucleic acid-adsorbing magnetic particles 43 together on the inner wall of the well 7. The pipette chip 42 sucks the residual solution without the nucleic acid-adsorbing magnetic particles 43, as shown in FIG. 7, and discharges the residual solution to a wastewater disposal section (not shown). After completion of the first PCR, the thermal cycle block may be cooled to about room temperature.

After the magnet 20 is moved away from the well 7, the cleaning liquid 103 is sucked through a hole cut in the film sealing the well 8 and transferred into the well 7. The mixture in the well 7 is stirred with the pipette chip 42, and the magnet 20 is raised again to collect the nucleic acid-adsorbing magnetic particles together on the inner wall of the well 7. The pipette chip 42 sucks the residual solution without the nucleic acid-adsorbing magnetic particles 43 (in the same state as shown in FIG. 7), and discharges the residual solution to the wastewater disposal section.

In the same manner, the ethanol 104 in the well 9 is transferred into the well 7, and the residual solution without nucleic acid-adsorbing magnetic particles 43 is sucked from the well 7 and discharged to the wastewater disposal section.

Cleaning in the course of purification is thus completed.

Finally, nucleic acids are extracted from the nucleic acid-adsorbing magnetic particles 43.

The liquid 102 in the well 7 and the eluant 105 in the well 10 are transferred into the well 6. After stirring the mixture and allowing it to stand, the magnetic particles are collected together by the magnet 20 in the same manner as in the cases using the cleaning liquid and ethanol. In this instance, nucleic acids are removed from magnetic particles, and the remaining solution contains the nucleic acids produced after the purification. A predetermined amount of this solution is sucked from the well 6 (in the same state as shown in FIG. 7) and transferred into the well 4. The film sealing the well 4 has been cut in advance.

Thus, the purification is completed.

Then, a hole is cut in the film sealing the well 11, and the solution 106 used for the second PCR is transferred into the well 4, followed by stirring with the pipette chip 42. After stirring, the second PCR is started in the state shown in FIG. 3. Since all the reagents have been consumed, the operation of the cooling block 24 may be stopped during the second PCR.

After completion of the second PCR, the top unit 26 and the cover 13 are brought into the state shown in FIG. 6, and the pipette chip 42 transfers the amplification product in the well 4 to the hybridizing section (not shown). After the transfer, the top unit 26 and the cover 13 are brought into the state shown in FIG. 3 again, then the support plate 32 is lowered, and the carriage 37 is shifted forward. In this state, the reaction/storage container 3 can be removed from the DNA testing apparatus.

As described with reference to FIG. 3, the solutions or reagents are previously placed in the reaction/storage container 3 in the order in which they are used and in which the pipette chip does not shift over unused wells (whose sealing film is not open) containing unused solutions, as much as possible. This minimizes the risk that the solutions or reagents drop into the unused wells even if the pipette chip spills a solution or reagent. Thus, adverse effects on the amplification and the purification can be eliminated.

Second Embodiment

Although the first embodiment uses a commercially available PCR microplate with wells arrayed at a pitch of 9 mm or its equivalent as the reaction/storage container, the reaction/storage container used in the present invention is not limited to this PCR microplate. The pitch of the wells, including recesses of the thermal cycle block and the cooling block, may be reduced or increased if necessary. The number of wells is not also limited to 96, and can be set according to the types of reagent and the number of analytes.

The wells may not be in a form of tapered cylinder, and may be in any form as long as the wells can come into tight contact with the thermal cycle block and the cooling block and purification can be performed.

Third Embodiment

Although the reaction/storage container 3 of the first embodiment contains only the reagents used for amplification, reagents used for other steps (of extraction, hybridization, and detection) may be contained.

In this instance, reagents that do not need temperature control or deteriorate by changes in temperature may be placed in wells between the cold storage section and the thermal cycle section.

Fourth Embodiment

The first embodiment uses magnetic particles and a magnet for purification, but a column filter may be used instead.

Figure 8:
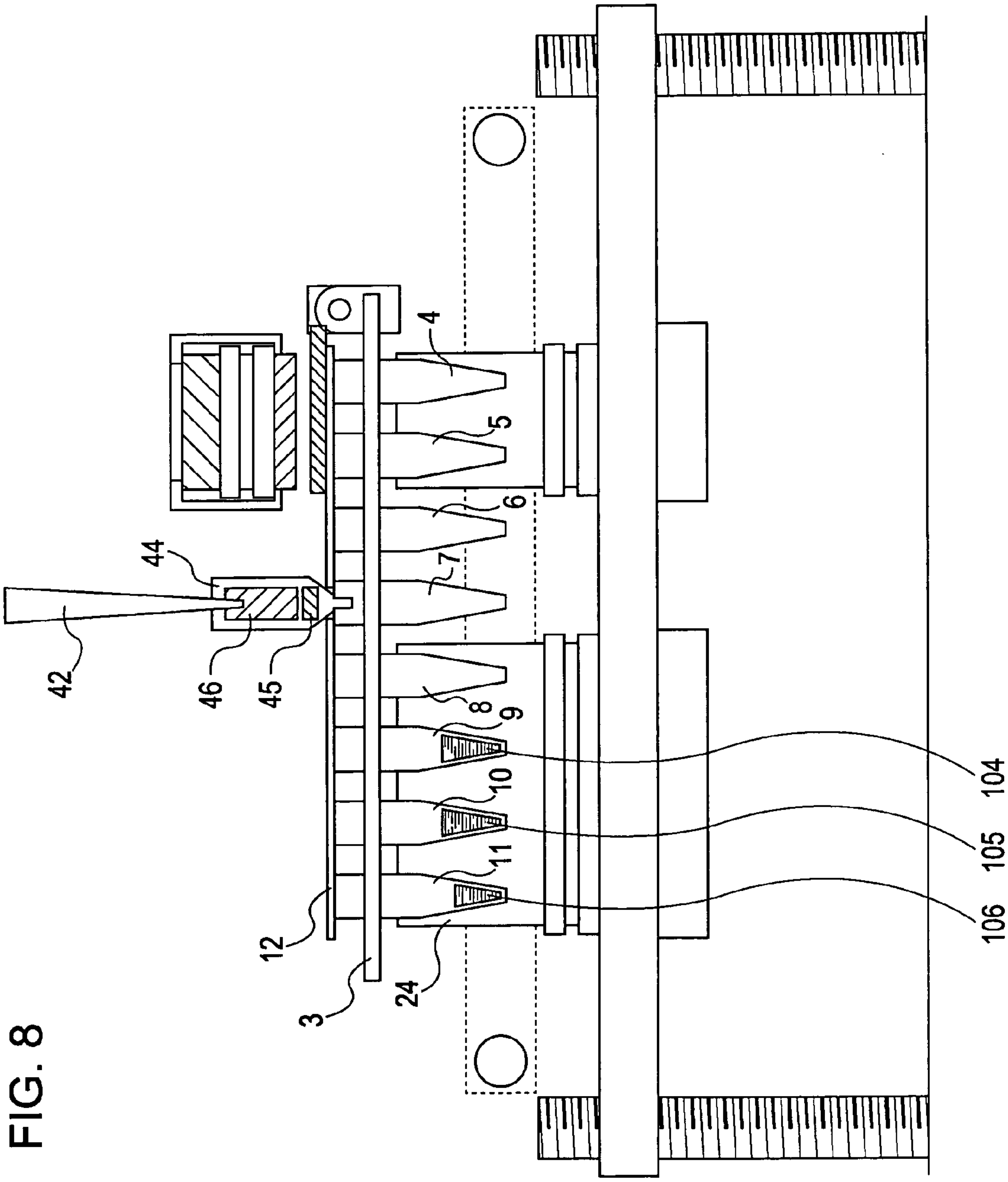
FIG. 8 is a front view of an amplifying section of a DNA testing apparatus according to a fourth embodiment of the present invention, in a state where a mixed solution is discharged into a column.
Figure 9:
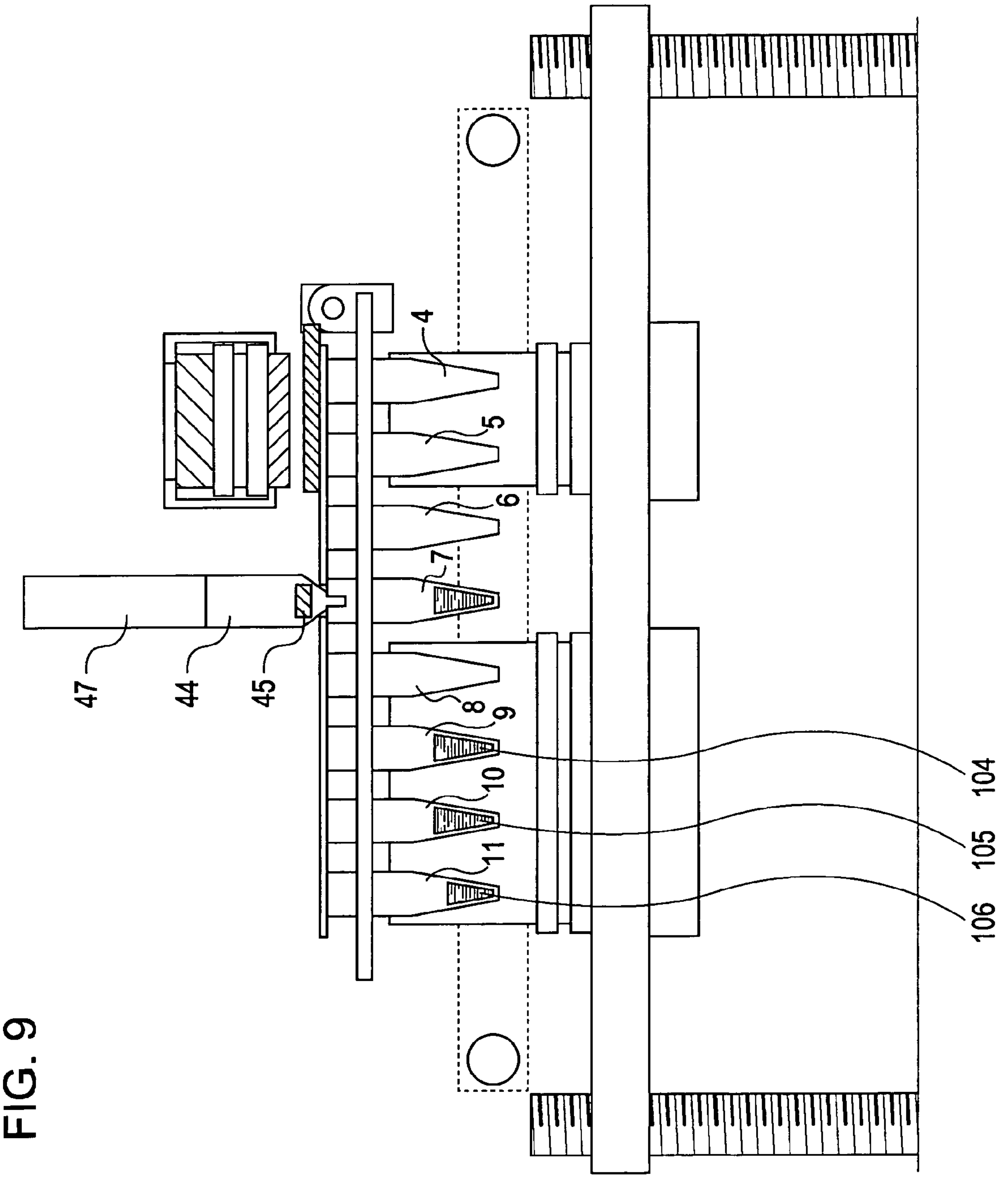
FIG. 9 is a front view of the amplifying section of the DNA testing apparatus according to the fourth embodiment, in a state where the mixed solution has passed through a filter.
Figure 10:
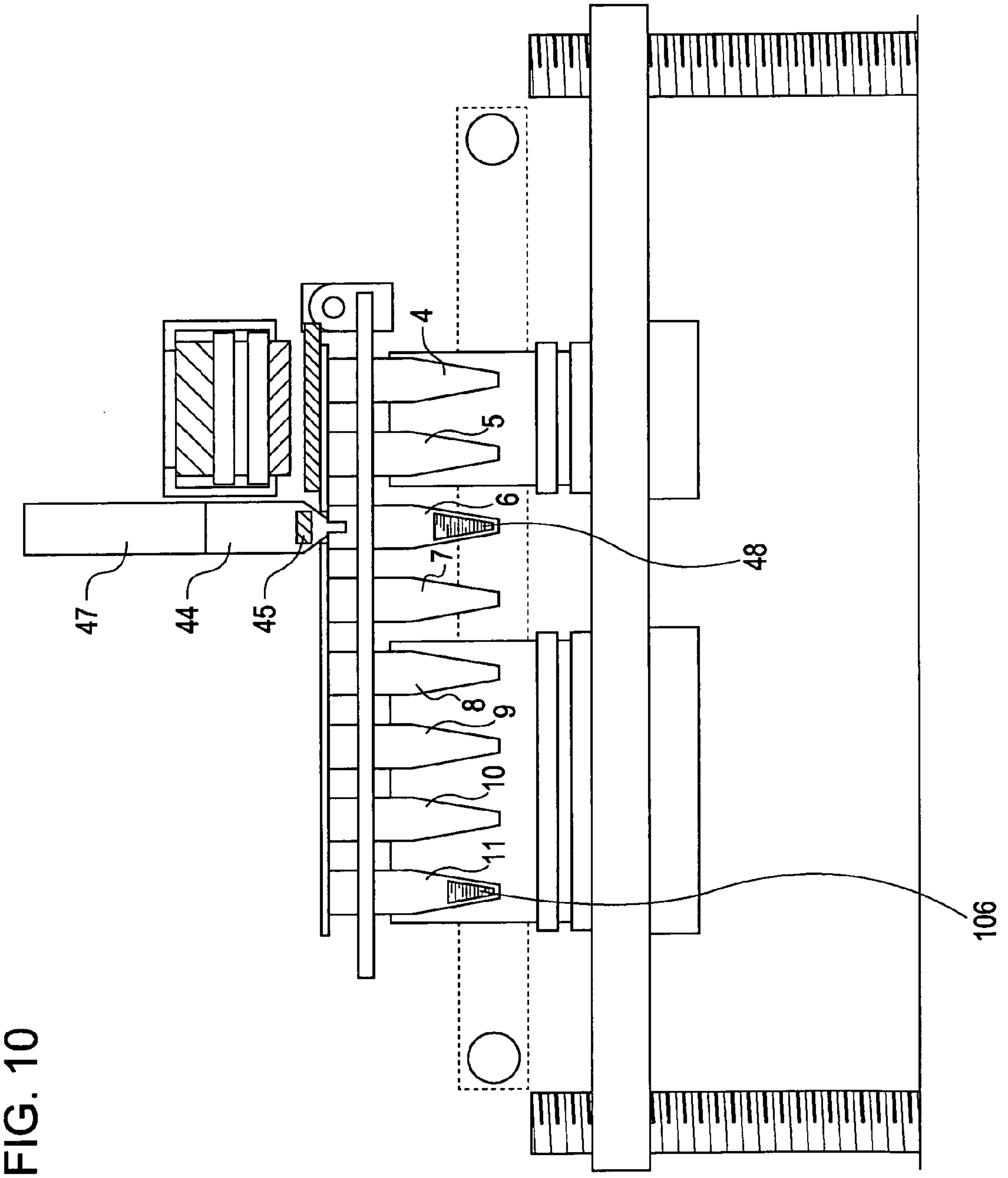
FIG. 10 is a front view of the amplifying section of the DNA testing apparatus according to the fourth embodiment, in a state where a nucleic acid solution is extracted to a well.

FIGS. 8 to 10 show an embodiment using a column filter. Some of the reference numerals representing the same parts are omitted from these figures.

In the present embodiment, the structure of the reaction/storage container 3 and the arrangement of the reagents are the same as in the first embodiment.

As shown in FIG. 8, purification is performed using column filters 44 each in which a filter 45 is fixed. After the first PCR, 12 column filters are each held over the corresponding well 7 in a line in the purifying section, using a driving mechanism (not shown). Then, the pipette chip 42 transfers the solution in the well 5 after the first PCR and the cleaning liquid in the well 8 into the column filter 44. FIG. 8 shows the state where the mixture 46 of the solution prepared by the first PCR and the cleaning liquid is placed in the column filter 44.

FIG. 9 shows the state where the mixture 46 has been passed through the filter 45 by applying pressure. A pressure pump 47 is brought into tight contact with the top of the column filter 44, using a driving mechanism (not shown), and applies pressure downward. Consequently, nucleic acids in the mixture 46 are adsorbed to the filter 45, and other components pass through the filter 45 to be collected in the well 7.

In the same manner as shown in FIGS. 8 and 9, ethanol in the well 9 is transferred into the column filter 44, and unwanted components are collected to the well 7 by applying pressure with the pressure pump 47.

Then, the column filter 44 is shifted over the well 6 and held there. After the eluant 105 in the well 10 is placed in the column filter 44, pressure is applied downward with the pressure pump 47 in tight contact with the top of the column filter 44 as shown in FIG. 10. Consequently, the nucleic acids adsorbed to the filter 45 are extracted, and collected together with the eluant into the well 6. The collected solution 48 is the nucleic acid purification product, and thus the purification is completed. The column filter 44 is moved away from the well 6, and the purification product 48 is drawn by the pipette chip.

The subsequent steps are performed in the same manner as in the first embodiment. Since in the present embodiment as well, the purifying section is located between the thermal cycle section and the cold storage section, the same effect can be produced.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2005-291298 filed Oct. 4, 2005, which is hereby incorporated by reference herein in its entirety.

What is claimed is:

1. A biochemical processing apparatus for performing biochemical processing in a container with a plurality of wells, the apparatus comprising:

a support constructed to support the container;

a heating mechanism constructed to heat a first plurality of wells, wherein the heating mechanism is disposed so as to oppose the first plurality of wells;

a cooling mechanism constructed to cool a second plurality of wells, wherein the cooling mechanism is disposed so as to oppose the second plurality of wells; and a processing mechanism constructed to perform a processing not requiring heating or cooling, the processing mechanism being disposed so as to oppose a third plurality of wells between the first plurality of wells and the second plurality of wells, wherein the heating mechanism, the processing mechanism, and the cooling mechanism are arranged in that order, and are opposed to the container supported by the support, and wherein the processing mechanism includes a magnetic member generating a magnetic field that is movably disposed and used for collecting magnetic particles, and the third plurality of wells contain the magnetic particles.

2. A biochemical processing apparatus for performing biochemical processing in a container with a plurality of wells, the apparatus comprising:

a support constructed to support the container;

a heating mechanism constructed to heat a first plurality of wells, wherein the heating mechanism is disposed so as to oppose the first plurality of wells;

a cooling mechanism constructed to cool a second plurality of wells, wherein the cooling mechanism is disposed so as to oppose the second plurality of wells; and a processing mechanism constructed to perform a processing not requiring heating or cooling, wherein the processing mechanism includes a column filter, and wherein the column filter is disposed above a third plurality of wells that are located between the first plurality of wells and the second plurality of wells.

* * * * *